US012618854B2

(12) United States Patent
Kooijman et al.

(10) Patent No.: US 12,618,854 B2
(45) Date of Patent: *May 5, 2026

(54) DIAGNOSTICS OF MILD OR ADVERSED PERIODONTITIS

(71) Applicant: KONINKLIJKE PHILIPS N.V., Eindhoven (NL)

(72) Inventors: Gerben Kooijman, Leende (NL); Amir Hussein Rmaile, Eindhoven (NL); Carl Glasse, Cambridge (GB); Marinus Karel Johannes De Jager, Eindhoven (NL); Iain Leslie Campbell Chapple, Birmingham (GB); Melissa Mackay Grant, Birmingham (GB); Philip Preshaw, Newcastle Upon Tyne (GB); John Taylor, Framlington Place (GB); Michael Alex Van Hartskamp, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 607 days.

This patent is subject to a terminal disclaimer.

(21) Appl. No.: 17/046,882

(22) PCT Filed: Apr. 10, 2019

(86) PCT No.: PCT/EP2019/059050
§ 371 (c)(1),
(2) Date: Oct. 12, 2020

(87) PCT Pub. No.: WO2019/197449
PCT Pub. Date: Oct. 17, 2019

(65) Prior Publication Data
US 2021/0148935 A1     May 20, 2021

(51) Int. Cl.
*G01N 33/68*          (2006.01)

(52) U.S. Cl.
CPC ... *G01N 33/6893* (2013.01); *G01N 2333/912* (2013.01); *G01N 2333/96494* (2013.01); *G01N 2800/18* (2013.01)

(58) Field of Classification Search
None
See application file for complete search history.

(56) References Cited

U.S. PATENT DOCUMENTS

2013/0183662 A1     7/2013  Zychlinsky et al.
2015/0219665 A1*    8/2015  Chapple ............. G01N 33/6893
                                                          506/18

FOREIGN PATENT DOCUMENTS

WO     WO-2004059293 A2 *  7/2004  ......... A61B 5/14546
WO            2016080777 A1  5/2016
                    (Continued)

OTHER PUBLICATIONS

Ebersole et al (Aging, inflammation, immunity and periodontal disease, Periodontol 2000, Oct. 2016;72(1):54-75). (Year: 2016).*
(Continued)

*Primary Examiner* — Bao-Thuy L Nguyen
*Assistant Examiner* — Chau N. B. Tran

(57)          ABSTRACT

Disclosed is an in vitro method for assessing whether a human patient suffering from periodontitis has mild periodontitis or advanced periodontitis. The method is based on the insight to determine a selection of two biomarker proteins. Accordingly, in a sample of saliva a patient suffering from periodontitis, the concentrations are measured of the proteins Pyruvate Kinase (PK) and at least one of Matrix metalloproteinase-9 (MMP9), S100 calcium-binding protein A8 (S100A8), and Hemoglobin subunit beta (Hb-beta); or of the proteins Matrix metalloproteinase-9 (MMP9) and at least one of S 100 calcium-binding protein A8 (S100A8) and S100 calcium-binding protein A9 (S100A9). Based on the concentrations as measured, a value is determined reflecting
(Continued)

the joint concentrations for said proteins. This value is compared with a threshold value reflecting in the same manner the joint concentrations associated with advanced periodontitis. The comparison allows assessing whether the testing value is indicative of the presence of advanced periodontitis or of mild periodontitis in said patient. Thereby, typically, a testing value reflecting a joint concentration below the joint concentration reflected by the threshold value is indicative for mild periodontitis in said patient, and a testing value reflecting a joint concentration at or above the joint concentration reflected by the threshold value, is indicative for advanced periodontitis in said patient.

24 Claims, 1 Drawing Sheet

(56) References Cited

FOREIGN PATENT DOCUMENTS

| | | | |
|---|---|---|---|
| WO | 2016095202 A1 | 6/2016 | |
| WO | 2017175673 A1 | 10/2017 | |

OTHER PUBLICATIONS

Tardif et al (Secretion of S100A8, S100A9, and S100A12 by Neutrophils Involves Reactive Oxygen Species and Potassium Efflux, J Immunol Res. 2015; 2015: 296149) (Year: 2015).*

Fuentes et al. (Emerging horizons of salivary diagnostics for periodontal disease, British Dental Journal vol. 217, No. 10, Nov. 21, 2014) (Year: 2014).*

Tsuchida et al. (Application of quantitative proteomic analysis using tandem mass tags for discovery and identification of novel biomarkers in periodontal disease, Proteomics 2013, 13, 2339-2350) (Year: 2013).*

Schwach-Abdellaoui et al. (Local delivery of antimicrobial agents for the treatment of periodontal diseases, European Journal of Pharmaceutics and Biopharmaceutics 50 (2000) 83+99) (Year: 2000).*

Murr et al. (Cross-Sectional Association of Salivary Proteins with Age, Sex, BodyMass Index, Smoking, and Education; J. Proteome Res. 2017, 16, 2273-2281). (Year: 2017).*

Cusabio (Human Pyruvate Kinase, M2-PK ELISA Kit, 2015) (Year: 2015).*

ALPCO Diagnostics (Alpha 1-Acid Glycoprotein ELISA, 2015) (Year: 2015).*

Santa Cruz Biotechnology (Hemoglobin β Antibody (21): sc-130321, 2017). (Year: 2017).*

Anil et al. (Hepatocyte Growth Factor Levels in the Saliva and Gingival Crevicular Fluid in Smokers with Periodontitis, Disease Markers vol. 2014, Article ID 146974, 6 pages) (Year: 2014).*

Hasan et al: "A Clinical Guide to Periodontology:Pathology of Periodontal Disease"; British Dental Journal, 2016, pp. 457-461.

PCT/EP2019/059050 ISR & WO, Aug. 23, 2019, 21 Page Document.

Giannobile et al: "Saliva as a Diagnostic Tool for Periodontal Disease: Current State and Future Directions": Periodoloty 2000, vol. 50, 2009, pp. 52-64.

Gursoy et al: "Salivary MMP-8, TIMP-1, and ICTP as Markers of Advanced Periodontitis": J Clin Periodontol 2010; 37: 487-493.

Krzsciak et al: "Relationship Between Pyruvate Kinase Activity and Cariogenic Biofilm Formation in Streptoccus mutans Biotypes in Caries Patients"; Infectious Diseases, a Section of the Journal Frontiers in Microbiology; Published May 16, 2017, 18 Page Document.

Nomura et al: "A New Screening Method for Periodontitis: an Alternative to the Community Periodontal Index": BMC Oral Health (2016), 16:64, 7 Oage Document.

Ramseier et al: "Identification of Pathogen and Host-Response Markers Correlated With Periodontal Disease"; J Periodontol, 2009, 80(3):436-446.

Sun et al: "Knockdown of PKM2 Suppresses Tumor Growth and Invasion in Lung Adenocarcinoma": Molecular Sciences, Published Oct. 15, 2015, pp. 24574-24587.

Todorovic et al: "Salivary Enzymes and Periodontal Disease"; Med Oral Patol Oral Cir Bucal 2006, E115-E118.

RAYBIO Label-Based (L-Series) Human Antibody Array 1000 Membrane Kit—A Combination of Human L-507 and Human L-493 Arrays, Feb. 2014.

Fuentes, L. et al. "Emerging horizons of salivary diagnostics for periodontal disease." British Dental Journal—vol. 217, No. 10, Nov. 21, 2014.

* cited by examiner

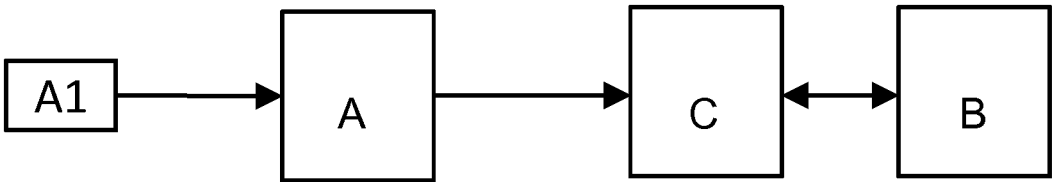

DIAGNOSTICS OF MILD OR ADVERSED PERIODONTITIS

CROSS-REFERENCE TO PRIOR APPLICATIONS

This application is the U.S. National Phase application under 35 U.S.C. § 371 of International Application No. PCT/EP2019/059050, filed on Apr. 10, 2019, which claims the benefit of European Patent Application No. 18166969.8, filed on Apr. 12, 2018. These applications are hereby incorporated by reference herein.

FIELD OF THE INVENTION

The invention is in the field of oral care, and pertains to saliva-based diagnostics of periodontal disease. Particularly, the invention pertains to a kit and method for distinguishing mild from advanced periodontitis.

BACKGROUND OF THE INVENTION

Gum inflammation, or gingivitis, is a non-destructive periodontal disease caused mainly by the adherence of dental bacterial biofilms, or dental plaque, to the tooth surface that triggers an inflammatory reaction in the surrounding tissue. Gingivitis is a reversible infection and inflammation of the gum tissues, and may be resolved with proper oral hygiene measures and dental professional intervention. If not detected or resolved, gingivitis usually leads to the inflammation of the tissues surrounding the tooth (i.e. periodontal tissues), a condition defined as periodontitis that causes tissue destruction and alveolar bone loss, and ultimately results in the loss of teeth. During the progression of gum disease, there are usually clinical signs and symptoms associated with it, such as the swelling of the gums, the change in color from pink to dark red, the bleeding of the gums, bad breath, and the gums becoming more tender or painful to touch.

Periodontitis is a chronic multifactorial inflammatory disease caused by oral microorganisms and characterized by progressive destruction of the hard (bone) and soft (periodontal ligament) tissues, ultimately leading to tooth mobility and loss. This is to be distinguished from gingivitis which is a reversible infection and inflammation of the gum tissues. Inflammatory periodontitis is one of the most prevalent chronic human diseases and a major cause of adult tooth loss. In addition to the substantial negative impact of periodontitis on oral health, there is also mounting evidence that periodontitis has systemic consequences and that it is a risk factor for several systemic diseases, including heart diseases (e.g. atherosclerosis, stroke), diabetes, pregnancy complications, rheumatoid arthritis and respiratory infections.

Early and accurate diagnosis of periodontal disease, thus, is important from both an oral and overall health perspective.

Periodontal diseases are still poorly diagnosed in general dental practice, resulting in relatively low rates of therapeutic intervention and significant amounts of untreated cases. Current diagnosis relies on imprecise, subjective clinical examination of oral tissue condition (color, swelling, extent of bleeding on probing, probing pocket depth; and bone loss from oral x-rays) by dental professionals. These conventional methods are time consuming, and some of the techniques used (pocket-depth, x-ray) reflect historic events, such as past disease activity, rather than current disease activity or susceptibility to further disease. Hence, more objective, faster, accurate, easier-to-use diagnostics which preferably may also be performed by non-specialists are desirable. Thereby it is desirable to measure current disease activity, and possibly a subject's susceptibility to further periodontal disease.

Saliva or oral fluids have long been advocated as a diagnostic fluid for oral and general diseases, and with the advent of miniaturized biosensors, also referred to as lab-on-a-chip, point of care diagnostics for rapid chair-side testing have gained greater scientific and clinical interest. Especially for periodontal disease detection, inflammatory biomarkers associated with tissue inflammation and breakdown may easily end up in saliva due to proximity, suggesting saliva has strong potential for periodontal disease detection. Indeed, this area thus has gained significant interest and encouraging results have been presented. For example, Kido et al. (J Periodont Res 2012; 47:488-499) identified 104 proteins in gingival crevicular fluid (GCF) samples from both healthy sites and sites of periodontitis, 64 proteins contained only in GCF from healthy sites and 63 proteins only in GCF from periodontitis sites. However, no definite test has emerged yet.

Biomarkers represent biological indicators that underpin clinical manifestations, and as such are objective measures by which to diagnose clinical outcomes of periodontal disease. Ultimately, proven biomarkers could be utilized to assess risk for future disease, to identify disease at the very earliest stages, to identify response to initial therapy, and to allow implementation of preventive strategies.

Previous limitations to the development of point-of-care tests for salivary biomarkers included a lack of technologies that were adaptable to chair-side applications and an inability to analyze multiple biomarkers in individual samples. Also the selection of which multiple biomarkers to include in such a test has not been adequately addressed in the literature nor implemented in practical tests.

Moreover, periodontitis can manifest itself across the entire spectrum of severity ranging from mild to advanced forms of the disease. In order to assess easily the severity of the condition, dentists often classify patients suffering from periodontitis into two groups—those suffering from mild periodontitis, and those suffering from advanced periodontitis. The available methods of making such an assessment, however, involve a labor intensive process that a dentist will not perform routinely on every patient and/or on every visit, and that is impossible to perform by a consumer (self-diagnosis).

It would be desired to provide a simpler process, and particularly a process that requires only that a small saliva sample is taken from a patient, and possibly by the patient him- or herself. It is desired that such a sample be entered into an in vitro diagnostic device, which will allow, based on measurement, a classification of the saliva sample such that it can return an indication of the likelihood that the patient is to be classified as suffering from mild periodontitis or as suffering from advanced periodontitis.

SUMMARY OF THE INVENTION

In order to better address the foregoing desires, the invention, in one aspect, concerns an in vitro method for assessing whether a human patient has mild periodontitis or advanced periodontitis, the method comprising detecting, in a sample of saliva from said human patient, the concentrations of the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

determining a testing value reflecting the joint concentrations determined for said proteins;

and comparing the testing value with a threshold value reflecting in the same manner the joint concentrations associated with advanced periodontitis, so as to assess whether the testing value is indicative for mild periodontitis or for advanced periodontitis in said patient.

In another aspect, the invention presents the use of the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

in a saliva sample of a human patient, as biomarkers for assessing whether the patient has mild periodontitis or advanced periodontitis.

Optionally, the age of the patient is also used as a biomarker.

In a further aspect, the invention resides in a system for assessing whether a human patient has mild periodontitis or advanced periodontitis, the system comprising:

detection means able and adapted to detect in a sample of saliva of the human patient the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9); and a processor able and adapted to determine from the determined concentrations of said proteins an indication of the patient having mild periodontitis or advanced periodontitis.

The system optionally contains a data connection to an interface, particularly a graphical user interface, capable of presenting information, preferably also capable of putting in information such as the age of the subject, as well as optionally other information such as sex and/or BMI (Body Mass Index), said interface being either a part of the system or a remote interface.

Optionally one or more of the foregoing items, particularly the processor, are enabled to function "in the cloud", i.e., not on a fixed machine, but by means of an internet-based application.

In a still further aspect, the invention provides a kit for detecting at least two biomarkers for periodontitis in a sample of saliva of a human patient, said kit comprising one or more, typically three or four, detection reagents for detecting:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9).

Typically, three or more detection reagents are used, for example four detection reagents, each of which binds a different biomarker. In one embodiment, a first detection reagent is for detecting PK, a second detection reagent is for detecting one of Matrix metalloproteinase-9 (MMP9), S100 calcium-binding protein A8 (S100A8), and Hemoglobin subunit beta (Hb-beta), and a third detection reagent is for detecting a different one of Matrix metalloproteinase-9 (MMP9), S100 calcium-binding protein A8 (S100A8), and Hemoglobin subunit beta (Hb-beta). An optional fourth detection reagent may be for detecting a further different protein from the group of Matrix metalloproteinase-9 (MMP9), S100 calcium-binding protein A8 (S100A8), and Hemoglobin subunit beta (Hb-beta). In another embodiment, the kit comprises at least two detection reagents, wherein a first detection reagent is for detecting MMP9 and a second detection reagent is for detecting S100A8 or S100A9.

In one embodiment, the invention provides a kit for detecting at least three biomarkers for periodontitis in a sample of saliva of a human patient, said kit comprising detection reagents for detecting Pyruvate Kinase (PK) and at least two of Matrix metalloproteinase-9 (MMP9), S100 calcium-binding protein A8 (S100A8), and Hemoglobin subunit beta (Hb-beta).

In yet another aspect, the invention provides an in vitro method for determining a change in status of periodontitis in a human patient suffering from periodontitis over a time interval from a first time point $t_1$ to a second time point $t_2$, the method comprising detecting, in at least one sample of saliva obtained from said patient at $t_1$ and in at least one sample of saliva obtained from said patient at $t_2$, the concentrations of the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

and comparing the concentrations, whereby a difference in any one, two or all three of the concentrations, reflects a change in status.

In a further aspect, the invention provides a method of diagnosing whether a human patient has mild periodontitis or advanced periodontitis, comprising detecting in a sample of saliva of the human patient the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

and assessing the presence of mild periodontitis or advanced periodontitis in the patient on the basis of the concentrations of said proteins in said sample. Optionally, the method of this aspect comprises the further step of treating the periodontitis in the patient.

In yet a further aspect, the invention provides a method of detecting the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

in a human patient suffering from mild or advanced peri-odontitis, comprising:

(a) obtaining a saliva sample from a human patient; and (b) detecting whether said proteins are present in the sample by contacting the sample with one or more detection reagents for binding said proteins and detecting binding between each protein and the one or more detection reagents. Typically, there is a first detection reagent for detecting PK, a second detection reagent for detecting one of Matrix metalloproteinase-9 (MMP9), S100 calcium-binding protein A8 (S100A8), and Hemoglobin subunit beta (Hb-beta), and a third detection reagent for detecting a different one of Matrix metalloproteinase-9 (MMP9), S100 calcium-binding protein A8 (S100A8), and Hemoglobin subunit beta (Hb-beta). In another embodiment, there is a first detection reagent is for detecting MMP9 and a second detection reagent is for detecting S100A8 or S100A9.

BRIEF DESCRIPTION OF THE DRAWINGS

FIG. 1 schematically represents a system for use in the method as described in this disclosure.

DETAILED DESCRIPTION OF THE INVENTION

In a general sense, the invention is based on the judicious insight that as few as two proteins can serve as biomarkers in a sample of saliva of a human patient suffering from periodontitis, for classifying said periodontitis as being in either of two categories, one category being advanced periodontitis, the other category being mild or moderate (i.e., not advanced, hereinbefore and hereinafter the term "mild periodontitis" will include moderate periodontitis, unless indicated otherwise). The latter category is hereinafter collectively indicated as mild periodontitis.

The identified protein biomarkers are Pyruvate Kinase (PK), Matrix metalloproteinase-9 (MMP9), S100 calcium-binding protein A8 (S100A8), Hemoglobin subunit beta (Hb-beta) and S100 calcium-binding protein A9 (S100A9). The following combinations of these proteins are used to diagnose gingivitis according to the invention:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9).

The subject's age may optionally be included as an additional marker.

Pyruvate kinase (PK) catalyses the final step of glycolysis. There are four tissue-specific isozymes of Pyruvate Kinase, each having particular kinetic properties needed for different tissues.

MMPs are a family of enzymes that are responsible for the degradation of extracellular matrix components such as collagen, proteoglycans, laminin, elastin, and fibronectin. They play a central role in the periodontal ligament (PDL) remodelling, both in physiological and pathological conditions. MMP-9, also known as 92 kDa type IV collagenase, 92 kDa gelatinase or gelatinase B (GELB), is a matrixin, a class of enzymes that belong to the zinc-metalloproteinases family involved in the degradation of the extracellular matrix.

S100 calcium binding protein A8 (S100A8) is a calcium- and zinc-binding protein which plays a prominent role in the regulation of inflammatory processes and immune response. It can induce neutrophil chemotaxis and adhesion.

Haemoglobin (Hb) is the iron-containing oxygen-transport metalloprotein in the red blood cells of nearly all vertebrates as well as the tissues of some invertebrates. Haemoglobin-beta (also known as beta globin, HBB, β-globin, and haemoglobin subunit beta) is a globin protein, which along with alpha globin (HBA), makes up the most common form of haemoglobin in adult humans, the HbA. Hb-β is typically 146 amino acids long and has a molecular weight of 15,867 Da. Normal adult human HbA is a heterotetramer consisting of two alpha chains and two beta chains. Hb-β is encoded by the HBB gene on human chromosome 11.

S100 calcium binding protein A9 (S100A9), also known as calgranulin B, is a calcium- and zinc-binding protein which plays a prominent role in the regulation of inflammatory processes and immune response. It can induce neutrophil chemotaxis, adhesion, can increase the bactericidal activity of neutrophils by promoting phagocytosis via activation of SYK, PI3K/AKT, and ERK1/2 and can induce degranulation of neutrophils by a MAPK-dependent mechanism.

The proteins mentioned above are known in the art. The skilled person is aware of their structure, and of methods to detect them in an aqueous sample, such as a saliva sample. Hereinafter the aforementioned protein biomarkers are collectively referred to as "the biomarker panels of the invention."

Table 1 in the Example provides 10 particularly preferred combinations according to the invention.

A biomarker panel of the invention, in one embodiment, comprises or consists of two, three, four or five protein biomarkers identified in the invention, i.e., PK, MMP9, S100A8, Hb-beta and S100A9. Preferably, a biomarker panel of the invention consists of not more than four of the protein biomarkers identified in the invention, e.g. PK plus Hb-beta, S100A8 and/or MMP9; or MMP9, S100A8 and S100A9. In addition to the biomarker panels of the invention, other biomarkers and or data, such as demographic data (e.g., age, sex) can be included in a set of data applied for the determination of the type of periodontitis.

An example of an additional protein biomarker is Matrix metalloproteinase-8 (MMP8). Another exemplary additional protein biomarker is Profilin. Hepatocyte Growth Factor (HGF) is a further possible additional protein biomarker. Free Light Chain Lambda (FLC-L) is another optional additional protein biomarker. Another exemplary additional protein biomarker is Alpha-1-acid glycoprotein (A1AGP). These proteins are included in some of the preferred biomarker panels in Table 1, below. Each of these proteins is known in the art.

MMP-8, also known as neutrophil collagenase or PMNL collagenase (MNL-CL), is a collagen protease enzyme which is present in the connective tissue of most mammals.

Profilin is an actin-binding protein involved in the dynamic turnover and restructuring of the actin cytoskeleton, found in most cells. It is important for spatially and temporally controlled growth of actin microfilaments, which is an essential process in cellular locomotion and cell shape changes. Human profilin-1 is typically 140 amino acids long when expressed but is often further processed into a mature form.

Hepatocyte Growth Factor (HGF) is a paracrine cellular growth, motility and morphogenic factor. It is secreted by mesenchymal cells and targets and acts primarily upon epithelial cells and endothelial cells, but also acts on hae-mopoietic progenitor cells. HGF has been shown to have a major role in myogenesis and in wound healing. Its ability to stimulate mitogenesis, cell motility, and matrix invasion gives it a central role in angiogenesis, tumorogenesis, and tissue regeneration. HGF stimulates growth of epithelial cells and prevents regeneration of the connective tissue attachment. HGF is known as a serum marker indicating disease activity in various diseases.

Free Light Chain proteins are immunoglobulin light chains. They are not associated with an immunoglobulin heavy chain. Unlike a typical whole immunoglobulin mol-ecule, a Free Light Chain protein is not covalently linked to an immunoglobulin heavy chain, e.g. the Free Light Chain is not disulphide bonded to a heavy chain. Typically the Free Light Chain comprises approximately 220 amino acids. Typically, the Free Light Chain protein comprises a variable region (often referred to as the Light Chain variable Region, $V_L$) and a constant region (often referred to as the Light Chain constant Region, $C_L$). Humans produce two types of immunoglobulin light chains, named with the letter kappa (κ) and lambda (λ). Each of these can be further divided into sub-groups based on variation in the variable region, with four kappa subtypes (Vκ1, Vκ2, Vκ3 and Vκ4) and six lambda subtypes (Vλ1, Vλ2, Vλ3, Vλ4, Vλ5 and Vλ6). Free Light Chain κ is typically monomeric. Free Light Chain λ is typically dimeric, linked by disulphide bonding (to another Free Light Chain λ). Polymeric forms of Free Light Chain λ and of Free Light Chain κ have been identified. Free light chains are produced by bone marrow and lymph node cells as well as locally in the periodontium by diffuse lympho-cytes, and are rapidly cleared from the blood and catabolised by the kidneys. Monomeric free light chains are cleared in 2-4 hours, and dimeric free light chains in 3-6 hours.

Alpha-1-acid glycoprotein (A1AGP) is a plasma alpha-globulin glycoprotein synthesized primarily by the liver. It is also sometimes known as Orosomucoid. It functions as a transport protein in the blood acts as a carrier of basic and neutrally charged lipohillic compounds. It is also believed to regulate the interaction between blood cells and endothelial cells.

Preferred extended biomarker panels comprise or consist of:

MMP8+MMP9+FLCλ+PK
MMP8+Hb-beta+PK+S100A8
HGF+MMP9+PK+S100A8
MMP9+A1AGP+PK+Hb-beta
Profilin+MMP9+PK+S100A8

When other biomarkers are optionally included, the total number of biomarkers (i.e. the biomarker panel of the invention plus other biomarkers) is typically 4,5 or 6.

However, a desirable advantage of the present invention is that the classification of periodontitis in a patient can be determined by measuring preferably not more than four biomarkers, and more preferably measuring only three bio-markers, with the biomarker panels of Table 1 (below) being preferred. Particularly, the determination does not need to involve the use of other data, which advantageously pro-vides a simple and straightforward diagnostic test.

The method, as desired, requires only that a small saliva sample, e.g. a dropsize, is taken from the subject. The size of the sample will typically range of from 0.1 µl to 2 ml, such as 1-2 ml, whereby smaller amounts, e.g., 0. 1 to 100 µl can be used for in vitro device processing, and whereby taking a larger sample, such as up to 20 ml, such as 7.5 to 17 ml, is also possible.

This sample is entered into an in vitro diagnostic device, which measures the concentrations of the at least two proteins involved, and which returns a diagnostic outcome, classifying the subject on the basis of a likelihood of having mild periodontitis or advanced periodontitis.

The ease of use of this invention will make it possible to test the majority of dental patients with periodontitis, or with a high risk for developing periodontitis, on a regular basis (e.g. as part of a regular dental check or even at home). This allows, inter alia, detecting the presence of mild periodon-titis before it proceeds to advanced periodontitis, and thus enables more timely taking oral care measures to prevent periodontitis from advancing. Or, e.g., with patients known to be at high risk for periodontitis, and tested for the first time, the method allows to identify whether the periodontitis is mild or advanced. Also, the method can be applied after treatment of a patient previously diagnosed with advanced periodontitis, in order to check whether the periodontitis has improved so as to become mild. In a further scenario, an indication that a patient previously suffering from mild periodontitis has not improved or has actually deteriorated after the start of the treatment regime, may lead to the dentist or patient deciding to alter the treatment plan to help expedite the recovery process. Particularly, the method is also suitable for self-diagnosis, whereby the steps of taking the sample and entering it into a device can be conducted by the patient him- or herself.

The patient may typically be known to have periodontitis when the invention is carried out to determine whether the periodontitis is mild or advanced. In certain embodiments therefore, the method is for assessing whether a human patient, known to have periodontitis, has mild periodontitis or advanced periodontitis.

A method of the invention typically comprises detecting the aforementioned at least two proteins making up a biomarker panel of the invention, and optional further bio-marker proteins, by using one or more detection reagents.

The "saliva" that is tested according to the invention may be undiluted saliva, which may be obtained by spitting or swabbing, or diluted saliva, which may be obtained by rinsing the mouth with a fluid. Diluted saliva may be obtained by the patient rinsing or swilling their mouth for a few seconds with sterile water (for example 5 ml or 10 ml) or other suitable fluid, and spitting into a container. Diluted saliva may sometimes be referred to as an oral rinse fluid.

By "detecting" is meant measuring, quantifying, scoring, or assaying the concentration of the biomarker proteins. Methods of evaluating biological compounds, including biomarker proteins, are known in the art. It is recognized that methods of detecting a protein biomarker include direct measurements and indirect measurements. One skilled in the art will be able to select an appropriate method of assaying a particular biomarker protein.

The term "concentration" with respect to the protein biomarkers is to be given its usual meaning, namely the abundance of the protein in a volume. Protein concentration is typically measured in mass per volume, most typically mg/ml or µg/ml, but sometimes as low as pg/ml. An alter-native measure is Molarity (or Molar concentration), mol/L or "M". The concentration can be determined by detecting the amount of protein in a sample of known, determined or pre-determined volume.

An alternative to determining the concentration is to determine the absolute amount of the protein biomarker in the sample, or determining the mass-fraction of the biomarker in the sample, for example the amount of the biomarker relative to the total of all other proteins in the sample.

A "detection reagent" is an agent or compound that specifically (or selectively) binds to, interacts with or detects the protein biomarker of interest. Such detection reagents may include, but are not limited to, an antibody, polyclonal antibody, or monoclonal antibody that preferentially binds the protein biomarker.

The phrase "specifically (or selectively) binds" or "specifically (or selectively) immunoreactive with," when referring to a detection reagent, refers to a binding reaction that is determinative of the presence of the protein biomarker in a heterogeneous population of proteins and other biologics. Thus, under designated immunoassay conditions, the specified detection reagent (e.g. antibody) binds to a particular protein at least two times the background and does not substantially bind in a significant amount to other proteins present in the sample. Specific binding under such conditions may require an antibody that is selected for its specificity for a particular protein. A variety of immunoassay formats may be used to select antibodies specifically immunoreactive with a particular protein. For example, solid-phase ELISA immunoassays (enzyme linked immunosorbent assay) are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice the background signal or noise and more typically more than 10 to 100 times the background.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region. The antibody may be a bispecific antibody, e.g. an antibody that has a first variable region that specifically binds to a first antigen and a second variable region that specifically binds to a second, different, antigen. Use of at least one bispecific antibody can reduce the number of detection reagents needed.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive.

The biomarker protein(s) of the invention can be detected in a sample by any means. Preferred methods for biomarker detection are antibody-based assays, protein array assays, mass spectrometry (MS) based assays, and (near) infrared spectroscopy based assays. For example, immunoassays, include but are not limited to competitive and non-competitive assay systems using techniques such as Western blots, radioimmunoassays, ELISA, "sandwich" immunoassays, immunoprecipitation assays, precipitin reactions, gel diffusion precipitin reactions, immunodiffusion assays, fluorescent immunoassays and the like. Such assays are routine and well known in the art. Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and re-suspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with Sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise.

ELISAs typically comprise preparing antigen (i.e. the biomarker protein of interest or fragment thereof), coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

Since multiple markers are used, a threshold is determined on the basis of the joint concentrations of these biomarkers (and optionally age). This threshold determines whether a patient is classified as having mild periodontitis or advanced periodontitis. The invention reflects the insight that periodontitis can be detected, as being mild or advanced, with sufficient accuracy based on a measurement of the combination of biomarkers as indicated above.

This insight supports another aspect, the invention, which is the use of the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

as biomarkers in a saliva sample of a human patient suffering from periodontitis, for assessing whether the patient has mild periodontitis or advanced periodontitis.

This use can be implemented in a method as substantially described hereinbefore and hereinafter.

The method of the invention comprises determining a testing value reflecting the joint concentrations measured for said proteins. A joint concentration value can be any value obtained by input of the concentrations as determined and an arithmetic operation of these values. This can, e.g., be a simple addition of the concentrations. It can also involve multiplying each concentration with a factor reflecting a desired weight of these concentrations, and then adding up the results. It can also involve multiplying the concentrations with each other, or any combination of multiplication, division, subtraction, exponentiation, and addition. It can further involve raising concentrations to some power.

Optionally, the testing value reflects the concentration of joint concentrations determined for said protein(s) in combination with the age of the subject.

The resulting joint concentration value is compared with a threshold value reflecting in the same manner the joint concentrations associated with the presence of advanced periodontitis. The comparison allows assessing whether the testing value is indicative of the presence of advanced periodontitis in the patients whose saliva is subjected to the test, or of mild periodontitis.

The threshold value can, e.g., be the joint concentration value, obtained in the same manner on the basis of the concentrations determined for the same proteins in a reference sample associated with the presence of advanced periodontitis, i.e. in a patient diagnosed with advanced periodontitis. Typically, thereby a value reflecting the same or higher joint concentration is indicative of the presence of advanced periodontitis in a tested patient. Analogously, a value reflecting a lower joint concentration in the saliva of a tested periodontitis patient, indicates that the periodontitis is mild or moderate (i.e., not advanced). However, it will be understood that it is also possible to calculate a threshold value (e.g. by using a negative multiplier) such that a testing value indicating advanced periodontitis would be below the threshold, and a testing value indicating mild periodontitis, would be above the threshold.

The threshold value can also be determined on the basis of measuring the concentrations of the present biomarker proteins in a set of samples, including patients with a known diagnosis of advanced periodontitis and not advanced (mild and/or moderate) periodontitis. Thereby the measured concentration values can be subjected to statistical analysis, possibly including machine learning methods, allowing to discriminate, with the desired sensitivity and specificity, patients classified as having mild or moderate periodontitis and patients classified as patients suffering from advanced periodontitis. Therefrom, the desired threshold value can be obtained. On the basis of this threshold value, a sample to be tested can be subjected to the same concentration measurement, and the concentration values are then processed, in the same manner in which the threshold value is obtained, so as to determine a joint concentration value that can be compared with the threshold, thus allowing the tested sample to be classified as having mild or advanced periodontitis.

In an interesting embodiment, the joint concentration value is obtained in the form of a score as follows. A numerical value (protein concentration values in e.g. ng/ml) is assigned to each measurement, and these values are used in a linear or non-linear combination to calculate a score between zero and one. In the event that the threshold value is determined on the basis of a set of subjects as mentioned above, the score between 0 and 1 is typically calculated with the sigmoid function that takes the joint concentration as input (as shown further on).

When the score exceeds a certain threshold, the method indicates that the patient has advanced periodontitis. The threshold may be chosen based on the desired sensitivity and specificity.

It will be understood that in performing a 'mild or advanced periodontitis classification' on a subject, in accordance with the invention, this is on subjects that can be assumed to suffer from periodontitis. This can either be known from e.g. a previously performed diagnosis of periodontitis, though perhaps without ability to differentiate the extent of it, or, e.g., assumed from the subject's oral health condition record.

Clinical definitions as acknowledged in the art are based on the following:

Gingival Index (GI)

A full mouth gingival index will be recorded based on the Lobene Modified Gingival Index (MGI) rated on a scale of 0 to 4, where:

0=absence of inflammation,

1=mild inflammation; slight change in color little change in texture of any portion of but not the entire margin or papillary gingival unit, 2=mild inflammation; but involving entire margin or papillary unit, 3=moderate inflammation; glazing, redness, oedema and/or hypertrophy of margin or papillary unit, 4=severe inflammation; marked redness, oedema and/or hypertrophy of marginal or papillary gingival unit, spontaneous bleeding, congestion, or ulceration].

Probing Depths (PD)

Probing depths will be recorded to the nearest mm using a manual UNC-15 periodontal probe. Probing depth is the distance from the probe tip (assumed to be at the base of the pocket) to the free gingival margin.

Gingival Recession (REC)

Gingival recession will be recorded to the nearest mm using a manual UNC-15 periodontal probe. Gingival recession is the distance from the free gingival margin to the cemento-enamel junction. Gingival recession will be indicated as a positive number and gingival overgrowth will be indicated as a negative number.

Clinical Attachment Loss (CAL)

Clinical attachment loss will be calculated as the sum of probing depth+recession at each site.

Bleeding on Probing (BOP)

Following probing, each site will be assessed for bleeding on probing, if bleeding occurs within 30 s of probing, a score of 1 will be assigned for the site, otherwise a score of 0 will be assigned.

The resulting subject group (patient group) definition is as follows, whereby the mild-moderate periodontitis group and the advanced periodontitis group are relevant to the present invention:

Healthy group (H): PD≤3 mm in all sites (but would allow up to four 4 mm pockets at distal of last standing molars), no sites with interproximal attachment loss, GI of ≥2.0 in ≤10% sites, % BOP scores≤10%;

Gingivitis group (G): GI≥3.0 in >30% of sites, no sites with interproximal attachment loss, no sites with PD>4 mm, % BOP scores>10%;

Mild-moderate periodontitis group (MP): interproximal PD of 5-7 mm, (equating to approximately 2-4 mm CAL) at ≥8 teeth, % BOP scores>30%;

Advanced periodontitis group (AP): interproximal PD of ≥7 mm, (equating to approximately ≥5 mm CAL) at ≥12 teeth, % BOP scores>30%.

In an embodiment, the method of the invention makes use of a system as represented schematically in FIG. 1. The system can be a single apparatus having various device components (units) integrated therein. The system can also have its various components, or some of these components, as separate apparatuses. The components shown in FIG. 1 are a measurement device (A), a graphical user interface (B) and a computer processing unit (C).

As mentioned above, the system of the invention comprises a data connection to an interface, whereby the interface itself can be a part of the system or can be a remote interface. The latter refers to the possibility to use a different apparatus, preferably a handheld apparatus such as a smartphone or a tablet computer, for providing the actual interface. The data connection in such cases will preferably involve wireless data transfer such as by Wi-Fi or Bluetooth, or by other techniques or standards.

The measurement device (A) is configured to receive a saliva sample, for example by putting a drop of saliva on a cartridge (A1), which can be inserted into the device (A). The device can be an existing device that is capable to determine, from the same saliva sample, the concentrations of at least the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9).

The measurement device (A) should be able to receive a saliva sample, for example by putting a drop of saliva on a cartridge (A1), which can be inserted into the device (A). The device may be an existing device that is capable to determine, from the same saliva sample, the concentrations of at least the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9).

The processing unit (C) receives numerical values for the protein concentrations from part (A). The unit (C) is provided with software (typically embedded software) allowing it to calculate a score (S) between 0 and 1. The software further includes a numerical value for the threshold (T). If the calculated value (S) exceeds (T), unit (C) will output an indication (I) of 'advanced periodontitis' to the GUI (B), otherwise it will output 'mild periodontitis'. A further embodiment may use the specific value of (S) to indicate the certainty with which the indication (I) is made. This can be a probability score, whereby 0.5 is a possible threshold value, and e.g. a score S=0.8 would indicate the probability of advanced periodontitis. Interesting options are:

Based on the score S, one can directly indicate a certainty, i.e. S=0.8 means 80% certainty of advanced periodontitis;

Based on the score S one can make a binary or tertiary indication:

S<T→mild periodontitis, S≥T→advanced periodontitis;

S<R1→mild periodontitis, R1≤S<R2→inconclusive, S≥R2→advanced periodontitis;

In addition, it is possible to attach a certainty to such a binary or tertiary indication. This certainty will be determined by the distance of the score S from the chosen threshold(s) (T,R1,R2).

A specific calculation of the score can be implemented, e.g., by means of a sigmoid function applying the following formula:

$$S = \frac{1}{1 + \exp\left(-\left(c_0 + \sum_{i=1}^{N} c_i B_i\right)\right)}$$

Therein N is the number of proteins/biomarkers used. $c_0$, $c_1$, etc. are coefficients (numerical values) and $B_1$, $B_2$, etc. are the respective protein concentrations.

Determining of the coefficients $c_i$ can be done by a training procedure:

Select N1 subjects with advanced periodontitis (e.g. as identified by a dentist using the current criteria) and N2 subjects with mild periodontitis.

The subjects without mild periodontitis are considered to have score S=0, the subjects with advanced periodontitis are considered to have score S=1.

Take a saliva sample from each subject and determine the protein concentrations of a combination of biomarkers as explained above.

Perform logistic regression between the protein concentrations and the scores.

Other regression or machine learning methods (linear regression, neural network, support vector machine) may be used to train a classifier that predicts whether a subject has gingivitis or a healthy oral condition based on the protein concentrations.

In particular, such a procedure has been applied (in the Example) using a clinical study with subjects having either mild periodontitis or advanced periodontitis (identified by clinical assessment by a dental professional via current criteria, e.g. American Academy of Periodontology criteria). Performance of various biomarker combinations were evaluated by means of Leave-1-out cross validation, resulting in the preferred biomarker combinations of the invention.

With reference to the aforementioned system, the invention also provides, in a further aspect, a system for assessing whether a human patient has mild periodontitis or advanced periodontitis, the system comprising:

> detection means able and adapted to detect in a sample of saliva of the human patient the proteins:

Pyruvate Kinase (PK) and at least one of Matrix metalloproteinase-9 (MMP9), S100 calcium-binding protein A8 (S100A8), and Hemoglobin subunit beta (Hb-beta); or > Matrix metalloproteinase-9 (MMP9) and at least one of S100 calcium-binding protein A8 (S100A8) and S100 calcium-binding protein A9 (S100A9);

As explained above, such means are known, and easily accessible to the skilled person;

Typically, there is provided a container for receiving an oral sample of a subject therein, the container provided with the detection means;

> a processor able and adapted to determine from the determined concentrations of said proteins an indication of the patient having mild periodontitis or advanced periodontitis.

Optionally, the system comprises a user interface (or a data connection to remote interface), particularly a graphical user interface (GUI), capable of presenting information; a GUI is a type of user interface that allows users to interact with electronic devices through graphical icons and visual indicators such as secondary notation, instead of text-based user interfaces, typed command labels or text navigation (none of such interface types being excluded in the present invention); GUIs are generally known, and are used typically in handheld mobile devices such as MP3 players, portable media players, gaming devices, smartphones and smaller household, office and industrial controls; as said, the interface optionally can also be chosen so as to be capable of putting in information, such as, e.g., the age of the subject, sex, BMI (Body Mass Index).

The invention also provides, either separately or as part of the aforementioned system, a kit for detecting at least two biomarkers for periodontitis in a sample of saliva of a human patient, said kit comprising one or more detection reagents for detecting:

> Pyruvate Kinase (PK) and at least one of Matrix metalloproteinase-9 (MMP9), S100 calcium-binding protein A8 (S100A8), and Hemoglobin subunit beta (Hb-beta); or
>
> Matrix metalloproteinase-9 (MMP9) and at least one of S100 calcium-binding protein A8 (S100A8) and S100 calcium-binding protein A9 (S100A9).

Typically, the kit comprises three detection reagents, each directed to a different biomarker, wherein a first detection reagent is for detecting PK, a second detection reagent is for detecting one of Matrix metalloproteinase-9 (MMP9), S100 calcium-binding protein A8 (S100A8), and Hemoglobin subunit beta (Hb-beta), and a third detection reagent is for detecting a different one of Matrix metalloproteinase-9 (MMP9), S100 calcium-binding protein A8 (S100A8), and Hemoglobin subunit beta (Hb-beta). In another embodiment, the kit comprises at least two detection reagents, wherein a first detection reagent is for detecting MMP9 and a second detection reagent is for detecting S100A8 or S100A9. There may be a third detection reagent in this embodiment, for detecting the other of S100A8 and S100A9. As discussed above with reference to the method of the invention, the kit may comprise more detection reagents, such as particularly for Profilin, A1AGP, FLC-lambda, HGF or MMP8, and/or for other proteins. In a preferred embodiment the detection reagents made available in the kit consist of the detection reagents for the selection of three proteins making up a 3-biomarker or 4-biomarker panel of the invention, as mentioned. In further embodiments, separate detection reagents are provided for each of the biomarker proteins present in a combination exemplified in Table 1 in the Example below.

Preferably said kits comprise a solid support, such as a chip, a microtiter plate or a bead or resin comprising said detection reagents. In some embodiments, the kits comprise mass spectrometry probes, such as ProteinChip™.

The kits may also provide washing solutions and/or detection reagents specific for either unbound detection reagent or for said biomarkers (sandwich type assay).

In an interesting aspect, the recognition of a biomarker panel of the invention is applied in monitoring the status of periodontitis in a human patient, over time. Accordingly, the invention also provides an in vitro method for determining a change in status of periodontitis in a human patient suffering from periodontitis over a time interval from a first time point $t_1$ to a second time point $t_2$, the method comprising detecting, in at least one sample of saliva obtained from said patient at $t_1$ and in at least one sample of saliva obtained from said patient at $t_2$, the concentrations of the proteins:

> Pyruvate Kinase (PK) and at least one of Matrix metalloproteinase-9 (MMP9), S100 calcium-binding protein A8 (S100A8), and Hemoglobin subunit beta (Hb-beta); or
>
> Matrix metalloproteinase-9 (MMP9) and at least one of S100 calcium-binding protein A8 (S100A8) and S100 calcium-binding protein A9 (S100A9);

and comparing the concentrations, whereby a difference of preferably at least two, and more preferably three concentrations, reflects a change in status. This difference can be reviewed as a difference in concentrations, thus allowing a direct comparison without first generating a number between 0 and 1, or any other classification. It will be understood that the measurements received at both points in time can also be processed in just the same manner as done when determining the mild or advanced periodontitis as above.

The invention also provides a method of diagnosing whether a human patient has mild periodontitis or advanced periodontitis, comprising detecting in the patient's saliva the presence of the proteins:

> Pyruvate Kinase (PK) and at least one of Matrix metalloproteinase-9 (MMP9), S100 calcium-binding protein A8 (S100A8), and Hemoglobin subunit beta (Hb-beta); or
>
> Matrix metalloproteinase-9 (MMP9) and at least one of S100 calcium-binding protein A8 (S100A8) and S100 calcium-binding protein A9 (S100A9).

The presence of mild periodontitis or advanced periodontitis in the patient is assessed on the basis of the concentrations of said proteins in said sample. Optionally, the method of this aspect comprises the further step of treating the periodontitis in the patient. This optional treatment step can comprise the administration of known therapeutic agents or dental procedures, or a combination of therapeutic agents and dental procedures. Known therapeutic agents include the administration of antimicrobial-containing agents such as a mouthwash, chip, gel or microsphere. A typical antimicrobial agent for use in treating periodontitis is chlorhexidine. Other therapeutic agents include antibiotics, typically orally-administered antibiotics, and enzyme suppressants such as doxycycline. Known non-surgical therapeutic procedures include scaling and root planing (SRP). Known surgical procedures include surgical pocket reduction, flap surgery, gum grafts or bone grafts.

The invention further provides a method of detecting the proteins:

Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9);

in a patient suffering from mild or advanced periodontitis, comprising:

(a) obtaining a saliva sample from a human patient; and (b) detecting whether said proteins are present in the saliva sample by contacting the saliva sample with a first, second and third detection reagent for detecting the proteins and detecting binding between each protein and detection reagent.

The invention will be further illustrated with reference to the following non-limiting example.

EXAMPLE

In a clinical study with 79 subjects, 41 of whom were diagnosed with mild periodontitis (including moderate periodontitis) and 38 with advanced periodontitis, ROC (Receiver-Operator-Characteristic) Area-Under-the Curve (AUC) values were obtained.

In statistics, a receiver operating characteristic curve, or ROC curve, is a graphical plot that illustrates the performance of a binary classifier system as its discrimination threshold is varied. The curve is created by plotting the true positive rate (TPR) against the false positive rate (FPR) at various threshold settings. The true-positive rate is also known as sensitivity, recall or probability of detection[1] in machine learning. The false-positive rate is also known as the fall-out or probability of false alarm and can be calculated as (1−specificity). The ROC curve is thus the sensitivity as a function of fall-out. In general, if the probability distributions for both detection and false alarm are known, the ROC curve can be generated by plotting for every value of the threshold, the value of the cumulative distribution function (area under the probability distribution from −∞ to the discrimination threshold) of the detection probability on the y-axis, versus the value of the cumulative distribution function of the false-alarm probability on the x-axis. The accuracy of the test depends on how well the test separates the group being tested into those with and without the disease in question. Accuracy is measured by the area under the ROC curve. An area of 1 represents a perfect test; an area of 0.5 represents a worthless test. A guide for classifying the accuracy of a diagnostic test is the traditional academic point system:

0.90-1=excellent (A)
0.80-0.90=good (B)
0.70-0.80=fair (C)
0.60-0.70=poor (D)
0.50-0.60=fail (F)

Based on the foregoing, in the results of the aforementioned clinical study, an ROC AUC value of above 0.75 is considered to represent a desirable accuracy for providing a diagnostic test in accordance with the invention.

The protein biomarkers explored are:

MMP8
MMP9
IL-1β
HGF
Free Light Chain (FLC) κ (kappa)
Free light chain (FLC) λ (lambda)
A1AGP
Hb-beta
Hb-delta
Keratin 4
Profilin
Pyruvate Kinase
S100A8
S100A9

Furthermore, in the employed logistic regression we considered as additional predictors κ+λ, κ−λ, κ/λ.

Additionally we included age as predictor.

This yields a total number of 4204 possible non-redundant panels, having at most 4 protein biomarkers (panel having only age is not considered). Non-redundant here means that a panel including e.g. κ+λ and κ−λ as predictors is not considered, as in the logistic regression it gives the same result as the corresponding panel including κ and λ as predictors.

Note that not restricting the number of protein markers in a panel, yields a number of 98302 possible non-redundant panels (panel having only age is not considered) given the predictors mentioned above.

From our study 184 panels, having at most 4 protein markers, were identified that provide AUC LOOCV>0.75 for classifying advanced periodontitis versus mild periodontitis. The preferred biomarker panels of the invention cover (at least) these 184 identified panels. Furthermore, of these 184 panels:

2 have only two protein markers
27 have three protein markers
155 have four protein markers The 2 panels containing only 2 protein markers are:

Pyruvate Kinase+MMP9 (AUC LOOCV=0.759)
Pyruvate Kinase+MMP9+Age (AUC LOOCV=0.788)

These panels are highlighted as preferred embodiments of the invention.

These data indicate that even two protein biomarkers (in the specified combinations) can provide an AUC LOOCV of >0.75 for classifying mild versus advanced periodontitis:

The 10 best performing panels have AUC LOOCV~0.79, as shown in Table 1 below. This summarizes, from among all biomarkers and biomarker panels determined, the data representing the best ROC AUC value for panels having at between two and four protein biomarkers.

TABLE 1

| MMP8 | IL1B | MMP9 | HGF | Age | κ | λ | κ + λ | κ/λ | κ − λ | A1AGP |
|---|---|---|---|---|---|---|---|---|---|---|
| X | | X | | X | X | | | | | |
| | | X | | X | | | | | | X |
| | | X | | X | | | | | | |
| | | X | | X | | | | | | X |
| | | X | | X | | | | | | |

TABLE 1-continued

| | | | | | | | |
|---|---|---|---|---|---|---|---|
| | X | X | X | | | | |
| | X | | X | | | | X |
| X | | | X | | | | |
| | X | | X | | | | |
| | X | | X | | | | |

| Hb-beta | Hb-delta | Keratin 4 | Profilin | Pyruvate Kinase | S100A8 | S100A9 | AUC LOOCV |
|---|---|---|---|---|---|---|---|
| | | | | X | | | 0.790 |
| | | | | X | | | 0.791 |
| X | | | | X | | | 0.790 |
| X | | | | X | | | 0.791 |
| | | | | X | X | | 0.794 |
| | | | | X | X | | 0.796 |
| | | | | X | X | | 0.789 |
| X | | | | X | X | | 0.792 |
| | | | X | X | X | | 0.790 |
| | | | | X | X | X | 0.790 |

Each of the biomarker combinations in this table is highlighted as a preferred combination of the invention. It can be seen that three of these panels have three protein markers, while seven panels have four protein markers. All panels use age as additional predictor, which may or may not be used according to the invention. These top-10 panels may be summarized as showing a preference for Pyruvate kinase and at least one of MMP9, or S100A8.

While the invention has been illustrated and described in detail in the drawings and foregoing description, such illustration and description are to be considered illustrative or exemplary and not restrictive; the invention is not limited to the disclosed embodiments. For example, it is possible to present detection reagents for different biomarkers in different units. Or, conveniently, a kit of the invention can comprise a fixed set of detection reagents for the protein biomarkers that are used in all embodiments, i.e., PK or MMP9, and flexible modules comprising a detection reagent for either of the further biomarkers, e.g., MMP9, S100A8, Hb-beta and S100A9.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose an in vitro method for assessing whether a human patient suffering from periodontitis has mild periodontitis or advanced periodontitis. The method is based on the insight to determine a selection of three biomarker proteins. Accordingly, in a sample of saliva a patient suffering from periodontitis, the concentrations are measured of the proteins: Pyruvate Kinase (PK) and at least one of Matrix metalloproteinase-9 (MMP9), S100 calcium-binding protein A8 (S100A8), and Hemoglobin subunit beta (Hb-beta); or Matrix metalloproteinase-9 (MMP9) and at least one of S100 calcium-binding protein A8 (S100A8) and S100 calcium-binding protein A9 (S100A9). Based on the concentrations as measured, a value is determined reflecting the joint concentrations for said proteins. This value is compared with a threshold value reflecting in the same manner the joint concentrations associated with advanced periodontitis. The comparison allows assessing whether the testing value is indicative of the presence of advanced periodontitis or of mild periodontitis in said patient. Thereby, typically, a testing value reflecting a joint concentration below the joint concentration reflected by the threshold value is indicative for mild periodontitis in said patient, and a testing value reflecting a joint concentration at or above the joint concentration reflected by the threshold value, is indicative for advanced periodontitis in said patient.

The invention claimed is:

1. A method for treating a human patient who has mild periodontitis or advanced periodontitis, wherein the method comprises:

detecting, in a sample of saliva from said human patient, the concentrations of the proteins: Pyruvate Kinase (PK) and Matrix metalloproteinase-9 (MMP9);

determining a testing value reflecting the joint concentrations determined for said proteins; and comparing said testing value with a threshold value reflecting in the same manner the joint concentrations associated with advanced periodontitis, so as to assess that the testing value is indicative for mild periodontitis or for advanced periodontitis in said patient; and administering, to the human patient for which the testing value is indicative for mild periodontitis or for advanced periodontitis, an anti-microbial therapeutic agent to the gum tissue of the human patient.

2. The method of claim 1, wherein the human patient is known to have periodontitis.

3. The method of claim 1, wherein an age of the subject is determined and the testing value reflects the joint concentrations determined for said proteins, in combination with the age of the subject.

4. The method of claim 3, wherein the proteins further comprise S100 calcium-binding protein A8 (S100A8).

5. The method of claim 3, wherein the proteins further comprise Hemoglobin subunit beta (Hb-beta).

6. The method of claim 1, wherein the threshold value is based on the concentrations determined for the proteins in one or more reference samples each sample associated with the presence of advanced periodontitis.

7. The method of claim 1, wherein the threshold value is based on the concentrations of the proteins in a set of samples, including samples from subjects that have mild or moderate periodontitis and samples from subjects having advanced periodontitis.

8. The method of claim 1, wherein the concentration values determined are arithmetically processed into a number between 0 and 1.

9. A method of treating a human patient who has mild periodontitis or advanced periodontitis, comprising;

detecting in a sample of saliva of the human patient the proteins: Pyruvate Kinase (PK) and Matrix metalloproteinase-9 (MMP9);

determining a testing value reflecting joint concentrations determined for said proteins; and assessing the presence of mild periodontitis or advanced periodontitis in the patient on the basis of the concentrations of said proteins in said sample, comprising comparing said determined testing value with a threshold value reflecting in the same manner the joint concentrations associated with advanced periodontitis, so as to assess whether the testing value is indicative for mild periodontitis or for advanced periodontitis in said patient; and administering, to the human patient for which the assessment is indicative for mild periodontitis or for advanced periodontitis, an anti-microbial therapeutic agent to the gum tissue of the human patient.

10. The method of claim 9, wherein the human patient is known to have periodontitis.

11. The method of claim 9, wherein an age of the subject is determined and the testing value reflects the joint concentrations determined for said proteins, in combination with the age of the subject.

12. The method of claim 11, wherein the proteins further comprise S100 calcium-binding protein A8 (S100A8).

13. The method of claim 11, wherein the proteins further comprise Hemoglobin subunit beta (Hb-beta).

14. The method of claim 9, wherein the threshold value is based on the concentrations determined for the proteins in one or more reference samples each sample associated with the presence of advanced periodontitis.

15. The method of claim 9, wherein the threshold value is based on the concentrations of the proteins in a set of samples, including samples from subjects that have mild or moderate periodontitis and samples from subjects having advanced periodontitis.

16. The method of claim 9, wherein the concentration values determined are arithmetically processed into a number between 0 and 1.

17. A method of treating periodontitis comprising:

detecting the proteins: Pyruvate Kinase (PK) and Matrix metalloproteinase-9 (MMP9) in a human patient, by:

(a) obtaining a saliva sample from a human patient; and (b) detecting whether the proteins are present in the sample by contacting the sample with one or more detection reagents for binding said proteins and detecting binding between each protein and the one or more detection reagents; and administering, to the human patient for which the proteins are detected in concentrations indicative for mild periodontitis or for advanced periodontitis, an anti-microbial therapeutic agent to the gum tissue of the human patient.

18. The method of claim 17, wherein the human patient is known to have periodontitis.

19. The method of claim 17, wherein an age of the subject is determined and the testing value reflects the joint concentrations determined for said proteins, in combination with the age of the subject.

20. The method of claim 19, wherein the proteins further comprise S100 calcium-binding protein A8 (S100A8).

21. The method of claim 19, wherein the proteins further comprise Hemoglobin subunit beta (Hb-beta).

22. The method of claim 17, wherein the threshold value is based on the concentrations determined for the proteins in one or more reference samples each sample associated with the presence of advanced periodontitis.

23. The method of claim 17, wherein the threshold value is based on the concentrations of the proteins in a set of samples, including samples from subjects that have mild or moderate periodontitis and samples from subjects having advanced periodontitis.

24. The method of claim 17, wherein the concentration values determined are arithmetically processed into a number between 0 and 1.

* * * * *